United States Patent [19]
Mochizuki et al.

[11] Patent Number: 5,452,070
[45] Date of Patent: Sep. 19, 1995

[54] METHOD FOR ANALYZING SOLID SAMPLE

[75] Inventors: Tadashi Mochizuki; Yohichi Ishibashi; Takanori Akiyoshi; Yoshihito Iwata; Satoshi Kinoshiro; Akiko Sakashita, all of Kawasaki, Japan

[73] Assignee: NKK Corporation, Tokyo, Japan

[21] Appl. No.: 266,239

[22] Filed: Jun. 27, 1994

[30] Foreign Application Priority Data

Jun. 29, 1993 [JP] Japan .................... 5-159416

[51] Int. Cl.$^6$ .............................................. G01N 1/04
[52] U.S. Cl. ................................................. 356/36
[58] Field of Search ......................................... 356/36

[56] References Cited

FOREIGN PATENT DOCUMENTS 3-118440  5/1991  Japan .

OTHER PUBLICATIONS

6th Process Technology Conference on Measurement and Control Instrumentation in the Iron and Steel Industry, Apr. 1985, Detroit, US. pp. 157–161, D. A. Cremers et al "Rapid Analysis of Steels Using Laser–Based Techniques".

Applied Spectroscopy, vol. 42, No. 7, 1988, Baltimore, US pp. 1231–1239–P. Arrowsmith et al "Entrainment and Transport of Laser Ablated Plumes for Subsequent Elemental Analysis".

Analytical Sciences, vol. 5, No. 5, Oct. 1989, pp. 535–538, T. Mochizuki et al, "Direct Analysis of Steels by Inductively Coupled Plasma Emission Spectrometry with a Q-Switched Neodymium: Yag Laser".

Analytical Sciences, vol. 7, No. 3, Jun. 1991, pp. 479–481, T. Mochizuki et al, "Selective Vaporization in Laser Ablation Solid Sampling for Inductively Coupled Plasma Atomic Emission and Mass Spectrometry of Steels".

"Rapid Analysis of Steels Using Laser-Based Techniques", D. A. Creme, 6th Process Technology Conference on Measurement and Control Instrumentation in the Iron and Steel Industry, Detroit, Mich., Apr. 14–17, 1985.

*Primary Examiner*—Vincent P. McGraw
*Attorney, Agent, or Firm*—Frishauf, Holtz, Goodman, Langer & Chick

[57] ABSTRACT

A method for analyzing solid sample comprises the steps of: introducing an inert carrier gas into a cell; a preliminary treatment step of irradiating laser beam to a sample surface of the solid sample in the inert carrier gas, the laser beam having a pulse half width of 0.001 $\mu$sec or more, a pulse energy density of 0.001 GW/cm$^2$ or more, and a frequency of 100 Hz or more; generating fine particles in the inert carrier gas on a condition that a rate of fine particles generation, V ($\mu$g/sec), and selection ratio, S, satisfy the following equations, the selection ratio being a retio of a concentration of a target element for analysis within the fine particles to a concentration of the target element for analysis within the solid sample;

$$S \leq 0.25 \log V + 1.5,$$

$$S \geq -0.2 \log V + 0.6,$$

$$0.1 \leq V \leq 100$$

intoducing the generated fine particles to a detector.

7 Claims, 6 Drawing Sheets

METHOD FOR ANALYZING SOLID SAMPLE

BACKROUND OF THE INVENTION

1. Field of the Invention

The present invention relates to a method for rapid analysis of solid sample made of metallic material or ceramic material, or the like and to a technology to improve the accuracy of analysis by laser vaporization through an optimization of the conditions for fine particle generation.

2. Description of the Related Arts

Along with the movement toward maintaining and improving quality, basic material industry dealing with metals and ceramics has strongly wanted the development of a material analysis method which is carried out quickly at a high accuracy. Responding to the request, an analysis by laser vaporization has been studied.

The analysis by laser vaporization started from the conventional analytical technology such as atomic absorption analysis and plasma emission analysis which determine the absorption spectra and emission spectra of elements in a solution by introducing the solution into an excitation flame, and extended the application to solid specimens. Accordingly, a solid target specimen is analyzed promptly by eliminating a step for liquefying the specimen. A proposed method for that purpose is the one where the solid specimen is vaporized to generate fine particles which are then introduced to an analytical device described above using a carrier gas to analyze the solid state elements by direct excitation thereof. The analytical device consists of a gas supply section, a fine particle generation section, and an element detection section, being attached with a data processing section and other auxiliary sections.

The solid specimen is sealed in a fine particle generation box, where the solid specimen is irradiated by laser rays in an inert gas flow. A part of the solid specimen becomes fine particles. The laser rays are easy for irradiating the solid specimen in a pulsed state while focusing on the surface of the specimen, and are capable of charging large amount of energy with a high density in a short time. By utilizing the energy, the laser rays which irradiate the surface of the solid specimen melt to emit or vaporize a part of the specimen to generate extremely fine particle samples. Even from a solid state specimen, the generated very fine particles are allowed to exist uniformly distributing in air, which uniformity is very close to that of a dissolved element in a solution.

However, the performed uniformity of the fine particles has not yet gave a sufficient accuracy of analysis compared with that in a solution specimen. One of the causes of inferior accuracy is the difficulty for generating a large quantity of fine particles. Responding to the issue, conditions for generating fine particles including the laser mode, the focusing of laser rays, and the laser oscillation frequency have been studied.

For example, "Rapid Analysis of Using Laser-based Techniques", D. A. Cremer, 6th Process Technology Conference on Measurement and Control Instrumentation in the Iron and Steel Industry, Detroit, Mich., Apr. 14–17, 1985 reported that a copper specimen being irradiated by laser rays of high oscillation frequency generated an increased amount of fine particles per unit time. Also the paper described that the specimen was placed on a rotating stage to transfer for responding to the reduction of the amount of generated fine particles with time after the start of laser ray irradiation. Another example, Japanese Unexamined Patent Publication No. 3-118440, disclosed an analytical device which used an XY stage to hold a specimen thereon to assure the movement of the specimen during the laser rays irradiation.

The above-described paper and device, however, pay insufficient consideration to the representative characteristics of the fine particle samples, and gave not sufficient accuracy in analysis of segregated elements and slight amount elements in the original solid specimen.

SUMMARY OF THE INVENTION

This invention was derived to solve the problem, and the object of this invention is to generate sufficient amount of fine particles and to improve the accuracy of analysis by assuring the representative characteristics of the fine particle samples.

To achieve the object, the present invention provides a method for analyzing solid sample which comprises the steps of:

positioning a solid sample in a cell;

introducing an inert carrier gas into the cell, said carrier gas having a carbon content of 1 ppm or less as impurity;

a preliminary treatment step of irradiating laser beam to a sample surface of the solid sample in the inert carrier gas, said laser beam having a pulse half width of 0.001 $\mu$sec or more, a pulse energy density of 0.001 GW/cm$^2$ or more, and a frequency of 100 Hz or more;

generating fine particles in the inert carrier gas on a condition that a rate of fine particles generation, V ($\mu$g/sec), and selection ratio, S, satisfy the following equations, the selection ratio being a retio of a concentration of a target element for analysis within the fine particles to a concentration of the target element for analysis within the solid sample;

$$S \leq 0.25 \log V + 1.5, \quad (1)$$

$$S \geq -0.2 \log V + 0.6, \quad (2)$$

$$0.1 \leq V \leq 100 \quad (3)$$

intoducing the generated fine particles to a detector; and analyzing the concentration of the target element within the fine particles.

DESCRIPTION OF THE PREFERRED EMBODIMENT

Figure 1:
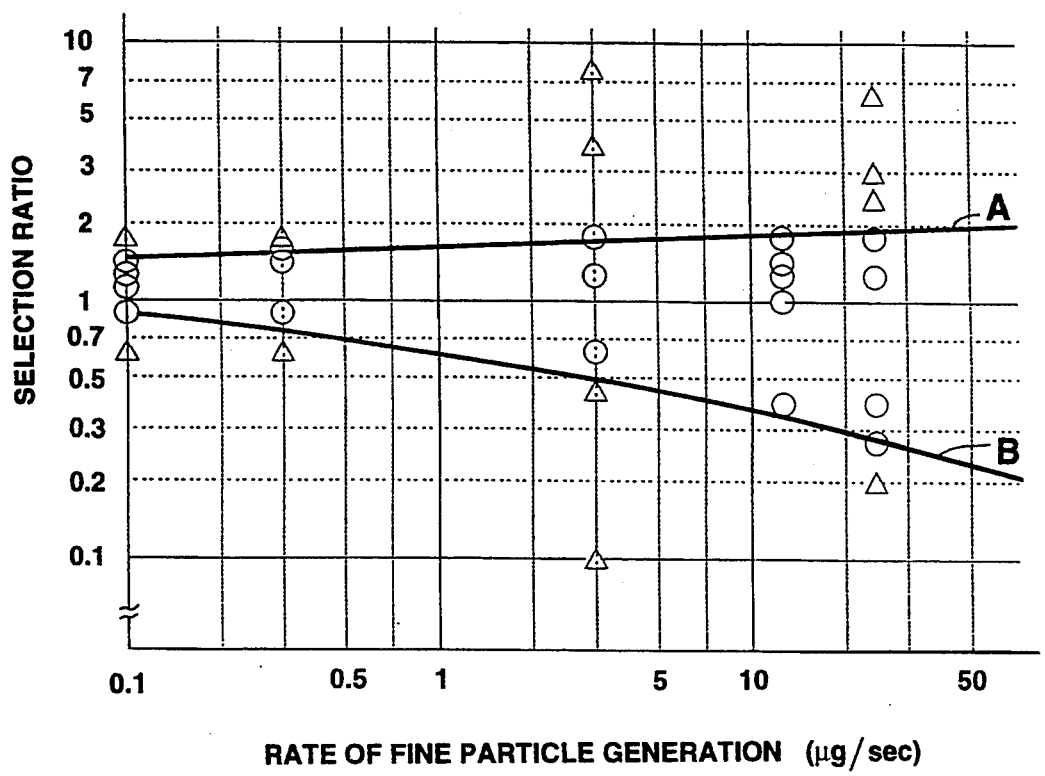
FIG. 1 shows the relation between the selection ratio of fine particles, the rate of fine particle generation, and the analytical accuracy, which is given to illustrate the principle of this invention.

The following consideration is given for the analysis by laser vaporization. When compared a solution sample which was prepared by dissolving a solid specimen to a solution based on a chemical quantitative ratio with a fine particle sample which was prepared by forming a part of the solid specimen into fine particles which were then transferred with a carrier gas, there found a difference between these samples in terms of quantity, uniformity, and identity with original specimen (hereinafter referred to simply as "the representative characteristics of specimen").

First, a solution sample can be prepared at a necessary amount by dissolving the specimen material in advance. On the contrary, a fine particle sample needs to provide while generating fine particles on the spot. When the rate of fine particle generation is low, an insufficient absolute sensitivity of applied instrument may appear.

As for the uniformity of the sample, a solution sample assures the uniformity because the elements exist in an ion state. However, a fine particle sample suffers a difference in size of individual particles and in segregation of carrier gas flow.

Regarding the representative characteristics of specimen, a solution sample dissolves all the solid specimen applied, but a fine particle sample tends to give a higher concentration of elements which easily become fine particles than the concentration in the original solid specimen and to give a lower concentration of elements which hardly become fine particles than that in the original solid specimen. For instance, when the elements have a large difference in boiling temperature each other, the element of lower boiling temperature selectively vaporizes. Consequently, the selection ratio is significantly affected by the state of selective vaporization.

Focusing on these differences, the inventors carried out detail studies on various factors relating to the representative characteristics of specimen and derived this invention. Regarding the size of individual particles among the above-described differences, a uniform particle size will be obtained to give nearly 1 μm of diameter inducing no coagulation under a condition of laser irradiation which maintains the rate of fine particle generation and the selection ratio in an adequate range. As for the segregation of the carrier gas flow, an internal standard is applicable for an effective correction. Consequently, it was found that the problem of the rate of fine particle generation and of the representative characteristics of specimen have the priority than the problem of the uniformity of specimen.

The problem of selective vaporization is a factor which significantly influences the representative characteristics of specimen. The selection ratio is defined as the ratio of the concentration of target element for analysis in the collected sample to the concentration of the element in the original specimen. Accordingly, the selection ratio of 1 is the ideal state, though an actual problem is how much deviation from unity may be acceptable. The accuracy of analysis relates to the selection ratio and the rate of fine particle generation. To maintain a high accuracy of analysis, only a small deviation of selection ratio is allowed in a system of relatively low rate of fine particle generation, and a large deviation of selection ratio is accepted in a system of increased rate of fine particle generation.

FIG. 1 shows an effect of the rate of fine particle generation and the selection ratio on the accuracy of analysis. The vertical axis is the selection ratio, and the horizontal axis is the rate of fine particle generation. The figure represents the relative deviation of element analysis for a standard steel specimen in terms of the elements contained in a range of from 0.01 to 1.0%. The symbol of open circle, (○), indicates the relative deviation of 5% or less, and the symbol of open triangle, (△), indicates the relative deviation of above 5%. A conventional analytical method gave the relative deviation on S and P in steel at 5% or more.

As seen in the figure, the open circles distribute between the boundary line A and the boundary line B, and the distance between these lines A and B broadens with the increase of rate of fine particle generation. For example, when the rate of fine particle generation is 0.1 μg/sec, the selection ratio has to be in a range from 0.8 to 1.25 for conducting the analysis of relative deviation within 5%, but the selection ratio ranging from 0.4 to 1.75 is acceptable at the rate of fine particle generation of 10 μg/sec. The boundary lines A and B are expressed by equations (1) and (2), respectively.

$$S \leq 0.25 \log V + 1.5, \quad (1)$$

$$S \geq -0.2 \log V + 0.6, \quad (2)$$

Since too small rate of fine particle generation may degrade the accuracy of analysis owing to an insufficient sensitivity of instrument for some content range of target element, the rate of fine particle generation is specified as 0.1 μg/sec or more. If the rate of fine particle generation exceeds 100 μg/sec, a degraded accuracy of detection may be induced caused from an enhanced contamination of excitation source of the detector or from an unstable excitation flame of plasma. Therefore, the upper limit of the rate of fine particle generation is specified as 100 μg/sec.

Since the rate of fine particle generation and the selection ratio depend on the pulse energy density, the half width of pulse, the oscillation frequency, etc., the rate is controllable using these conditions. Nevertheless, an increase of rate of fine particle generation may affect the selection ratio. To avoid an influence which may degrade the accuracy of analysis, the relation between the rate of fine particle generation, V (μg/sec), and the selection ratio, S, has to satisfy the equations (1), (2), and (3). In other word, the maintaining these equations allows a precision analysis by laser vaporization.

$$S \leq 0.25 \log V + 1.5, \tag{1}$$

$$S \geq -0.2 \log V + 0.6, \tag{2}$$

$$0.1 \leq V \leq 100 \tag{3}$$

The result shown in FIG. 1 is applicable also for metals, minerals, ceramics, and other materials, as well as the steel specimen. Furthermore, a melted specimen shows the same trends as in the solid specimen. However, some elements included in these specimens, which elements showed the relative standard deviation within 5%, stayed always near to 5%, and some gave very low value of relative standard deviation. Investigation revealed that the elements giving a large relative deviation were the elements being contained in the metallic material and having a strong tendency to segregation (hereinafter referred to simply as "the segregation elements") or the elements of slight content, and that the elements which uniformly distributed were those of uniform solid solution.

When the fine particle generation is performed on a local area on a solid specimen, the segregation elements show a strong effect of segregation. The effect is, however, buffered by broadening the surface area for generation. The means to broaden the generation area include the widening of beam diameter of laser rays and the sweeping action of the laser beam. A widened laser beam decreases the energy density per irradiated area, so the method has a limitation. Therefore, the method of beam sweep for moving the focusing point is superior.

When a laser beam having the beam diameter of 100 $\mu$m is used for irradiation while moving the focusing point at a rate of 1 mm/sec, the irradiation area per sec. becomes 10 times that obtained by a stationary focusing point.

A moving focusing point gives another effect. Repeated irradiation of beam while fixing the focusing point forms a hole having the diameter of beam width on the surface of specimen, and the gathered samples come from the bottom of the hole. Consequently, the distance between the focusing lens and the irradiation plane changes with time, and the sample generation plane becomes out of focus, then the emitted substance becomes hard to diffuse and the quantity of generating fine particles decreases. A moving focusing point prevents the disadvantage and enhances the rate of fine particle generation. Regarding the relation between the rate of fine particle generation and the transfer speed of focusing point, the rate of fine particle generation depends also on the pulse energy density and the oscillation frequency. The relation is given in FIG. 2.

Figure 2:
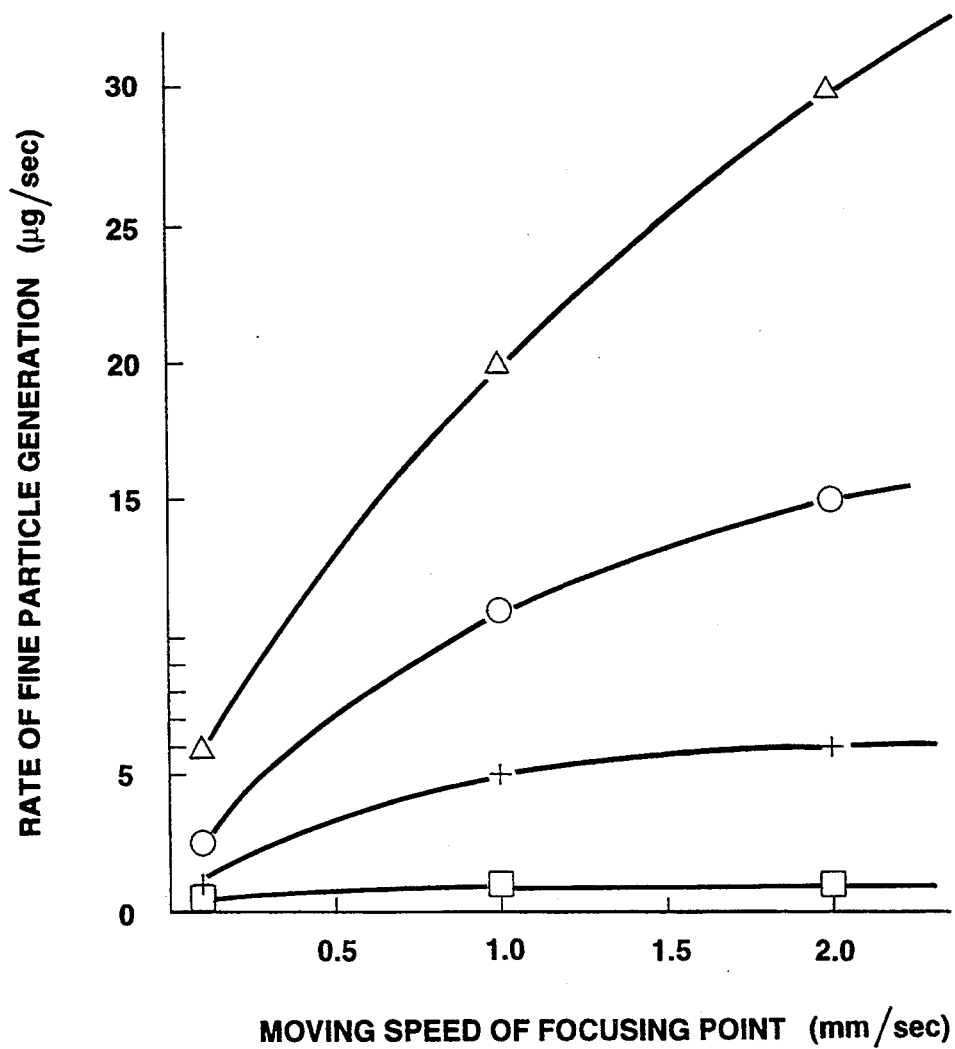
FIG. 2 shows the relation between the transfer speed of focusing point and the rate of fine particle generation, which is given to explain the conditions of laser irradiation.

The vertical axis of FIG. 2 is the rate of fine particle generation, and the horizontal axis is the transfer speed of focusing point. The graph shows the relation of these variables at an pulse energy density of 1 GW/cm$^2$ and an oscillation frequency of 10 Hz (open square symbol, □), 100 Hz (cross symbol, +), 1 KHz (open circle symbol, ○), and 10 KHz (open triangle symbol, △). The effect of the transfer speed of focusing point appears strongly with the increase of oscillation frequency. The rate of fine particle generation saturates in a region of small transfer speed of focusing point when the oscillation frequency is low.

Also for the segregation elements, to maintain the relative standard deviation within 2%, the rate of fine particle generation is preferably at 0.1 $\mu$g/sec or more, and preferably the pulse energy density is 0.01 GW/cm$^2$ or more, the oscillation frequency of 100 Hz or more, and the transfer speed of focusing point of 0.1 mm/sec or more. In that preferred case, the rate of fine particle generation becomes 1 $\mu$g/sec or more. The value is considered necessary to eliminate the effect of segregation, though the value is considerably larger than 1 $\mu$g/sec which is a required level for the case of 5% or less of the relative standard deviation of segregation elements.

When the oscillation frequency is increased, and the moving speed of focusing point is increased, the saturation point of the rate of fine particle generation becomes high. Further preferable condition is prepared at the oscillation frequency of 500 Hz or more and the transfer speed of focusing point of 1 mm/sec or more to obtain the fine particles stably at a rate of 10 $\mu$g/sec or more. The condition allows to determine a slight amount of segregation element at a content of 0.01% or less with a high accuracy.

Increase of pulse energy density increases the rate of fine particle generation to an adequate range. Over the optimum range, however, a different phenomenon appears and no energy is consumed to generate fine particles any more. The approximate limit of the optimum range is 50 GW/cm$^2$. Beyond the range, the atmospheric gas becomes plasma owing to the electro-magnetic or thermal action of the laser rays, which plasma consumes the energy to induce a drastic reduction of the rate of fine particle generation. If the pulse energy density is below 0.01 GW/cm$^2$, the rate of fine particle generation decreases and the selective vaporization is enhanced.

Figure 3:
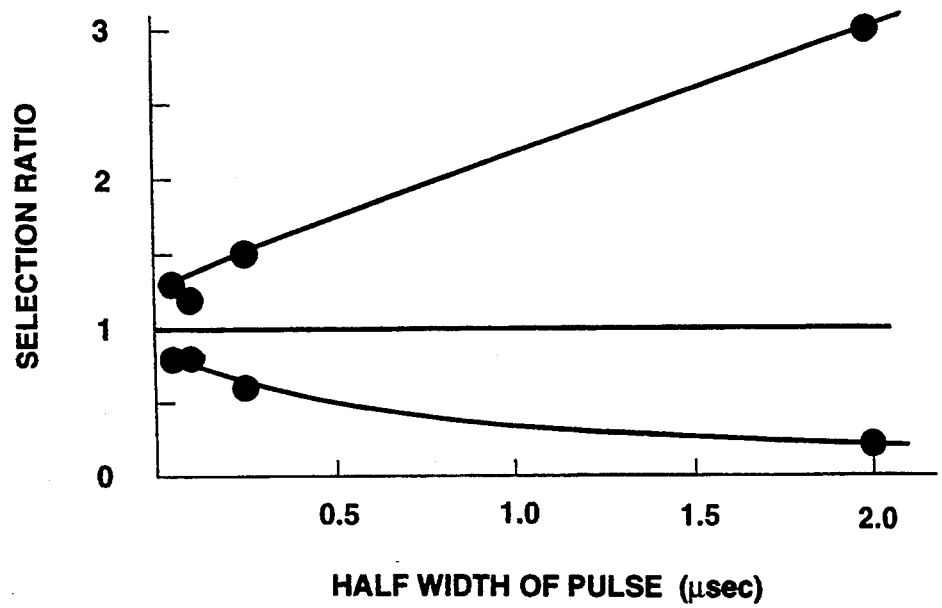
FIG. 3 shows the relation between the half width of pulse and the selection ratio, which is given to explain the conditions of laser irradiation.

The selective vaporization is affected most significantly by the pulse width. When laser rays are applied within a short time to emit the fine particles of solid specimen, the selection ratio decreases. As an example, a solid specimen containing both Mn having a low boiling point and Mo having a high boiling point was irradiated by laser rays having a pulse energy density of $1 \times 10^7$ W/cm$^2$ at a frequency of 100 Hz while varying the half width of pulse to determine the change of selection ratio. The result is given in FIG. 3. The vertical axis is the selection ratio, and the horizontal axis is the half width of pulse. Longer half width of pulse makes the selection ratio away from unity. However, a half width of pulse at 0.5 $\mu$sec or less keeps the selection ratio in a range of from 0.6 to 1.6. Longer half width of pulse increases the zone receiving the thermal influence on the solid specimen, and the fraction of fine particle generation through vaporization presumably increases.

Figure 4:
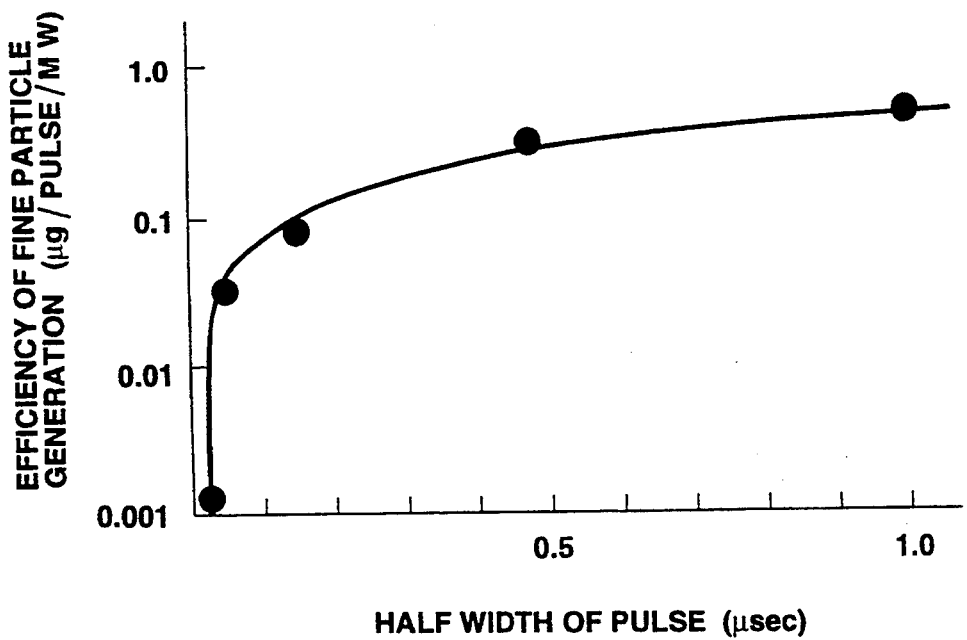
FIG. 4 shows the relation between the half width of pulse and the rate of fine particle generation, which is given to explain the conditions of laser irradiation.

In this manner, a shortened half width of pulse improves the selection ratio. Nevertheless, the shortening of half width of pulse has a limitation. FIG. 4 gives an example of observed efficiency of rate of fine particle generation per pulse. The vertical axis is the generation efficiency defined as the amount of fine particle generated per pulse divided by the applied energy (megawatt). The horizontal axis is the half width of pulse. When the half width of pulse becomes below 0.05 $\mu$sec, the efficiency suddenly decreases. Furthermore, when a half width of pulse is shortened to apply a necessary quantity of energy, the wave height of the pulse is required to increase to compensate the shortened half width, which results in a sharp pulse pattern. A sharp pulse tends to induce the plasma-forming phenomenon in atmosphere described before. Accordingly, an adequate value of the half width of pulse is 0.05 $\mu$sec or more.

As described above, to cope with the reduction of selection ratio and with the segregation of elements, a preferred mode to secure the amount of fine particle generated is the irradiation of laser rays having a half width of pulse ranging from 0.05 to 0.5 $\mu$sec under the conditions of the energy density ranging from 0.01 to 50 $GW/cm^2$, and the oscillation frequency of 100 Hz or more onto the solid specimen, while transferring the focusing point at a rate of 0.1 mm/sec or more. This mode allows the analysis of segregation elements within an accuracy of relative standard deviation of 2%. In that case, elements which do not induce segregation are naturally analyzed with a higher accuracy. The transfer speed of focusing point is easily increased by a transfer method which is described later. In particular, the transfer speed of 1 mm/sec or more is most preferable for a slight amount element.

The movement of focusing point may be done by transferring the solid specimen, and may be done by sweeping the beam. For the case that a solid specimen moves at a speed of several hundred meters per minute, which is seen in a steel strip plating line, the former transfer method may be applied. In the case of stationary solid specimen, the latter transfer method is superior because the method easily performs a quick movement. The latter method is most preferable for a large specimen and for a heavy specimen.

An analysis by laser vaporization generally adopts the range of sweeping within several millimeters, which range is narrower than that of laser beam machining. For instance, at a transfer speed of 1 mm/sec, when the focusing point travels in zigzag pattern to cover 1 mm range with 10 go-and-back cycles at a spacing of 100 $\mu$m, the range of sweep becomes 1 $mm^2$.

A practical method of beam sweep is the galvanometer method which uses the rotation of two reflection mirrors and an f$\theta$ lens. This method has been used in laser beam machining and provides a range of sweeping as wide as several tens of centimeters. The method, however, has a poor focusing degree and needs a considerably large oscillator to maintain the energy density of 0.01 $GW/cm^2$. In this regard, the inventors studied a means to move the focusing point at a high speed without inducing the degradation of pulse energy density, and found that, as far as the moving range of several millimeters square which is necessary for the analysis by laser vaporization, the linkage of the rotating single reflection mirror and the horizontal movement of a single-focus lens achieved the performance.

Movement of focusing point is actuated either by rotating a refection mirror or by transferring the focusing lens. Combination of these means increases the speed of movement. FIG. 5 illustrates the principle of these means.

Figures 5A, 5B, 5C:
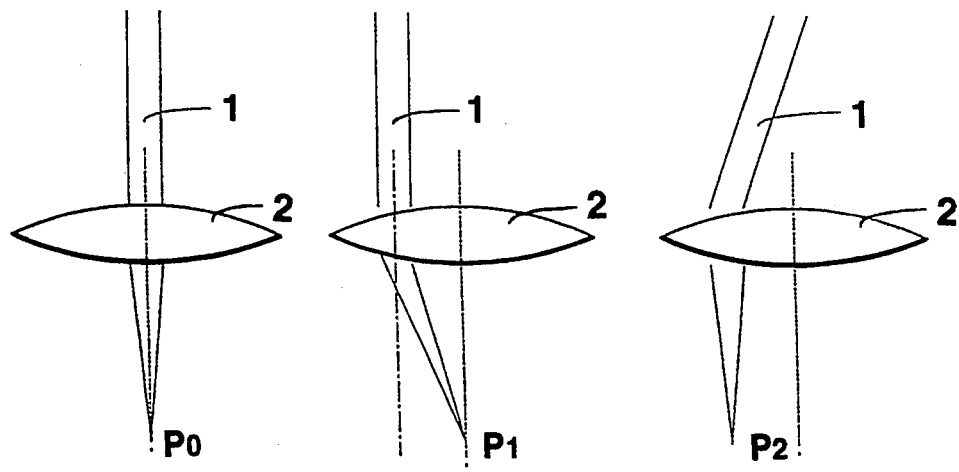
FIGS. 5(A)–5(C) show the relation between the parallel movement of focusing lens and the focusing point, which is given to explain the method of transfer of the focusing point.

FIG. 5(A) shows a normal use of lens, where the parallel incident light 1 of laser rays is adjusted by a reflection mirror (not shown) and is guided vertically to the center of the focusing lens 2. In that case, the focusing point $P_o$ matches the focus of the focusing lens 2. When the focusing lens 2 is moved from the state of FIG. 5(A) rightward vertically to the light axis, the state becomes to FIG. 5(B). In that case, the incident light 1 enters the focusing lens 2 at a point deviated leftward by the distance of the movement of focusing lens 2, not entering the center of the focusing lens 2.

Nevertheless, the focusing point $P_1$ matches the focus of the focusing lens 2. Since the focusing lens 2 has moved rightward, the focusing point $P_1$ has also moved rightward by the same distance. FIG. 5(C) shows the case that the reflection mirror is rotated while the focusing lens 2 does not move. In that case, the incident light enters the focusing lens along the inclined axis, not vertically, and the point of enter shows a drift from the center of lens. Accordingly, the focusing point $P_2$ does not match the focus of the focusing lens 2 and moves by the distance corresponding to the inclination of incident light.

As a result, the movement of lens or the rotation of reflection mirror can move the focusing point. In addition, when the focusing lens moves parallel to the sample generation plane, the distance between the lens and the focusing point is equal to the focusing distance and it remains unchanged.

Therefore, if the fine particle collecting section of an analytical device by laser vaporization is provided with an irradiation point transfer device having a mechanism which moves the laser ray focusing lens in parallel to the specimen surface and having a mechanism which rotates the reflection mirror, then the movement of focusing point becomes easy under a state of sharp focusing onto the specimen surface. The movement of focusing point while maintaining the sharply focused state is an important thing in an analysis by laser vaporization. If the degree of focusing is reduced by the movement of focusing point, the rate of fine particle generation and the selection ratio suffer a bad influence.

The parallel movement of a focusing lens is easily done in two-axial directions. Solely the parallel movement of the focusing lens may transfer the focusing point, and the parallel movement is combined with the rotation of the reflection mirror allows further easy response to the requirement of high speed transfer and of sweep locus. For example, if a mechanism is capable of rotating the reflection mirror around an axis parallel to the irradiation plane and of transferring the focusing lens in axial direction, then the analytical device becomes simple and utilizes efficiently the fine particle generation surface.

Adding to the selective vaporization and the elemental segregation, the contamination is another variable to degrade the representative characteristics of original specimen. There are two sources of the contaminants: one is the original specimen, and the other is the carrier gas. The former contamination is resulted by sampling also the foreign matter attached to the original specimen for analysis. That type of foreign matter includes dust and dirt, and oxides yielded on the surface, gaseous substances such as $CO_2$ and hydrocarbons adsorbed on the specimen.

Since the fine particle samples are taken from the surface layer of specimen, they are strongly influenced by the contamination of the surface. The surface of an original specimen is often cleaned before the analysis. Nevertheless, it is unavoidably subjected to oxidation to some degree and to contamination by components in air or suspended particles before being introduced into the fine particle sampling device. The contaminants in air include chemical compounds of hydrocarbons, calcium, sulfur, phosphorus, aluminum, etc. Even when the rate of fine particle generation is at 10 $\mu$g/sec, the generated fine particles are carried by the carrier gas flowing at an approximate rate of 1 l/min, so a component included in the specimen at a content of 0.01 wt. % is sent to the detection section at a concentration below 0.1 wt.ppm. Therefore, a contaminant existed in air at a very slight amount can not be overlooked, and the specimen is necessary to be cleaned by a highly purified inert atmosphere immediately before generating the fine particle samples.

Irradiation of laser rays onto a solid specimen induces the generation of fine particles firstly from the top surface layer which contains contaminants. Diffusion of the contaminants including oxides into the original specimen to change the composition of original specimen shall be avoided, though the condition of irradiation during the first stage is not restricted by the conditions to prevent the selective vaporization and removing the surface layer at the original composition.

In this respect, the conditions for irradiation at the measurement are the optimum conditions for cleaning. Different from the measuring period, however, there is no need for considering the concentration necessary to obtain a certain level of sensitivity, so the rate of fine particle generation becomes not a significant variable. The lower limit of half width of pulse and of energy density become a moderate level, and the upper limit of them is unnecessary to define. A preferable condition for practical application is the half width of pulse 0.001 $\mu$sec or more, the pulse energy density 0.001 GW or more, and the oscillation frequency 100 Hz or more. The transfer speed of focusing point is unnecessary to limit. Nevertheless, since the whole surface area for generating fine particle samples is required to be cleaned, the surface area allocated for the generation of fine particle samples is subjected to sweep-irradiation for a necessary period of cleaning.

When the irradiation is carried out while introducing a carrier gas, the carrier gas carries away the contaminants which are emitted from the specimen surface as fine particles. Following the laser ray irradiation for several seconds aiming at the surface cleaning, the measurement is carried out without influence of contaminants. The obtained representative characteristics of the specimen are further improved.

The contaminants coming from carrier gas include the impurities in the carrier gas itself and those entered during the flow passage of carrier gas. The use of carrier gas after purifying to eliminate impurities as far as possible is the same practice used in the purification of solvent in the case of solution specimen. A solvent is rarely contaminated on route of flow passage. However, a transporting gas quite often encounters the contamination during its transfer passage. The gas supply section also feeds Ar and $N_2$ for plasma flame, air for atomic absorption flame, acetylene and nitrous oxide for excitation flame of the element detection section. Although the gas for excitation flame is smaller in volume than the carrier gas, it is also purified similar to the carrier gas to prevent the contamination in the flow passage.

For the gas purification purpose, a gas purifying device is attached to the gas supply section of an analytical device by laser vaporization to eliminate the impurities in the gas applied, at need. The gas purifying system is made by a material having a low reactivity with and low adsorption capacity to impurities in gas and having a high heat durability and being easily cleaned by heating.

A He gas commercially available at a purity of 99.99999% may often be used without further purification. However, Ar gas of 99.99% purity and $N_2$ gas of 99.999% purity often undergo further purification before use.

As the gas purification device, a metallic getter gas purification device may be used. Commercially available high purity Ar gas has a purity of 99.995%, but that kind of Ar gas includes hydrocarbon gas and contains the impurity carbon at around several ppm. The carbon content corresponds to several times that in a low carbon steel, so the gas needs to be purified further and needs to be protected from recontamination in the succeeding pipeline. As for the determination of components, the impurities in gas is subtracted as blank value, so the concentration of the impurities is not necessarily lowered than the concentration level of target component. Nevertheless, a high blank value degrades the accuracy of analysis.

A series of experiments which were carried out under a varied condition for the generation of the particles revealed that an accurate analysis of a low carbon steel needed to suppress the impurity concentration in gas to 1 ppm or lower level. As for the purification ability of a getter, the experiments also showed that finely powdered Zr metal with sufficient purification thereof allowed for the getter to purify the high purity Ar further to a level of 0.2 ppm carbon concentration.

The gas piping may use metals such as stainless steel and aluminum, or non-porous ceramics such as glass. The important precautions for piping include the prevention of invasion of outside gas at joint section while maintaining easy cleaning configuration of the joint. The seal material may use a heat-resistant synthetic rubber containing fluorine. However, sealing materials unavoidably inferior in the cleanliness to metallic or ceramic materials, so the seals are necessary to minimize the surface area.

For simplicity in description, the above discussion was given using a solid specimen. The analytical method is also applicable for molten specimen. For a molten specimen, however, the segregation and the pores left after the generation of fine particles are not necessary to consider. So the focusing point is not needed to move during the measurement.

Examples of the molten specimen include a molten metal at smelting, and zinc, tin, aluminum, etc. of hot dip coating.

EXAMPLE

A solid specimen was irradiated by laser rays to generate fine particles which were then introduced to an excitation flame using a carrier gas to analyze.

The target specimens for analysis were carbon steel, stainless steel, aluminum alloy, titanium alloy, ceramic material, and copper alloy. Table 1 lists the composition of these specimens.

EXAMPLE-1

A carbon steel was analyzed by emission analysis using an inductively coupled plasma (hereinafter referred to simply as "ICP").

Figure 6:
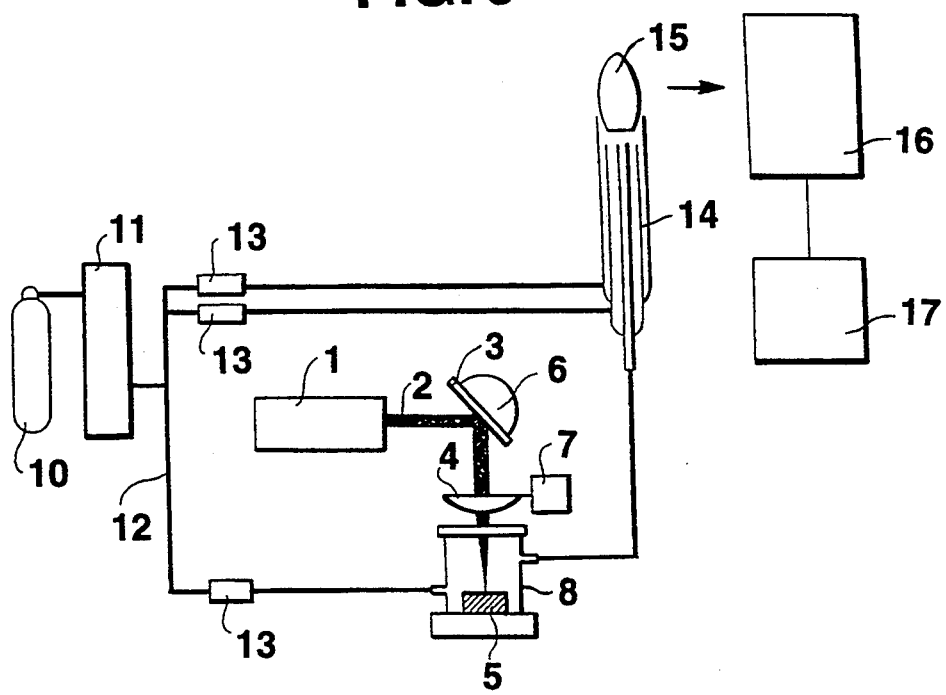
FIG. 6 shows a conceptual drawing of the laser vaporization analyzer used in an Example of this invention.

The device of ICP applied is shown in FIG. 6. The laser rays 2 emitted from the laser oscillator 1 is adjusted their proceeding direction by the reflection mirror 3, focused by the focusing lens 4, then guided to irradiate onto the solid specimen 5. The reflection mirror 3 is rotated by the rotary mechanism 6, and the focusing lens 4 is movable by the parallel transfer mechanism 7.

Figure 9:
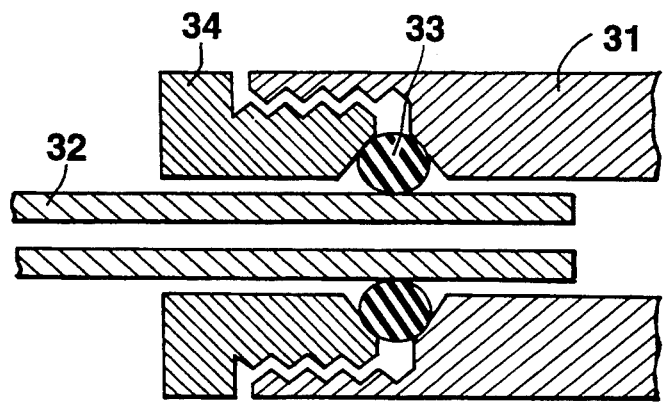
FIG. 9 shows a lateral cross sectional view of a joint used in the piping of an Example of this invention.

The solid specimen 5 was placed in the irradiation cell 8, and the carrier gas was introduced to the cell 8. The gas supplied from the gas cylinder 10 was purified at the purification device 11, at need, and was sent to the laser irradiation cell 8 or the high frequency induction plasma torch 14 via the piping system 12. A Zr getter purification device was used as the purification device 11. The piping system 12 was provided with a mass flow regulator 13 to control the gas flow rate. Stainless steel was used for the piping, and glass was used for the laser irradiation cell 8 and the plasma torch 14. The joint of these components was done by the joint illustrated in FIG. 9. A metallic pipe 31 had a threaded inside step, and the step received a "Viton" O ring 32 which was made from a heat-resistant synthetic rubber containing fluorine. Then a glass tube 33 was inserted in the O ring, and the threaded closure 34 was fitted to the metallic pipe 31. The O ring 32 is pressed by the threaded closure 34 to become an elliptical section, which attached tightly to the inner face of the metallic pipe 31 and the outer face of the glass tube 33 to secure the air tightness.

High purity Ar gas was used as the carrier gas and the flame gas. The laser oscillator employed an ultrasonic Q switch Nd; YAG laser, Ruby laser, EXIMA laser, and $CO_2$ laser.

Figure 7:
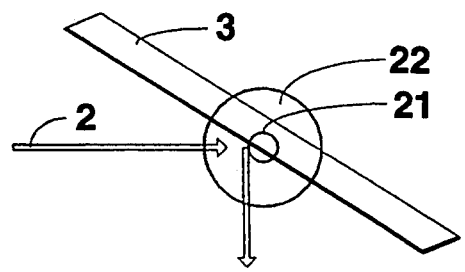
FIG. 7 shows a conceptual drawing of the rotary device illustrating the method to rotate the reflection mirror, which is given to explain the method of transfer of the focusing point.
Figure 8:
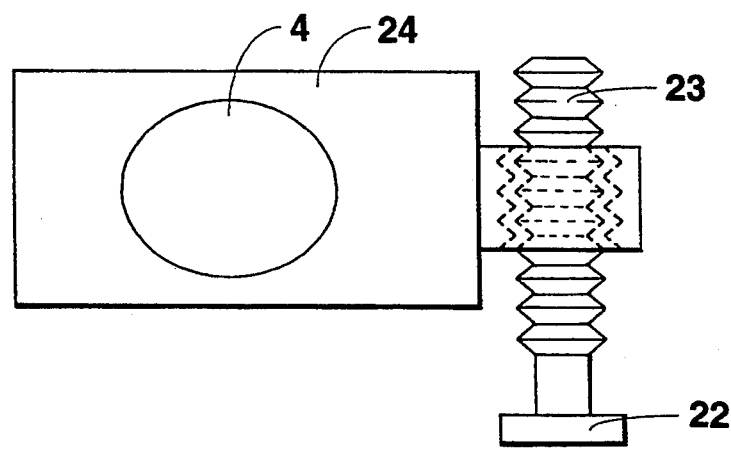
FIG. 8 shows a conceptual drawing of the transfer device illustrating the parallel movement of the focusing lens, which is given to explain the method of transfer of the focusing point.

Transfer of the focusing point was carried out by the combination of the rotation of the reflection mirror and the parallel movement of the focusing lens. For the rotation of reflection mirror, as seen in FIG. 7, the rotary axis 21 was linked with the step motor 22, and the rotational angle was set corresponding to the distance from the reflection point to the focusing lens, and the direction of rotation was changed using the frequency ranging from 1 to 100 Hz. As for the parallel movement of lens, as illustrated in FIG. 8, the step motor 22 was used to rotate the rotary press rod 23 having a male thread on it, and the rotational movement of the rotary press rod 23 was changed to the linear movement of the lens table 24 having a female thread on it. The speed of the transfer was in a range of from 1 to 100 mm per minute. The direction of lens movement matched the rotational axis of the reflection mirror, and the moving directions of individual focusing points induced by the rotation of the reflection mirror and by the movement of focusing lens cross each other at right angle.

The preliminary treatment was carried out by the sweep of laser rays having the beam diameter of 200 μm within a range of 2 mm square under the condition of half width of pulse 100 μsec, energy density 0.005 GW, oscillation frequency 5000 Hz.

Other than the Examples of this invention, Comparative Examples using a condition outside of the scope of the invention and Comparative Examples employing a conventional method were also tested to compare each other.

Table 2 shows the conditions of laser vaporization and the analytical results.

Examples of this invention gave the analytical values of relative standard deviation within 5% for all elements analyzed.

Among those Examples, Test No. 1 through 6 which satisfied the conditions of superior mode including half width of pulse, energy density, oscillation frequency, and transfer speed of focusing point showed particularly good results giving relative standard deviation within 2%, except for extremely low B content (Test No. 2). Also for B, when the transfer speed of focusing point exceeds 1 mm/sec, the relative standard deviation became within 2%.

Test No. 7 through 10 came outside of the specified condition for superior mode in each item of energy density (Test No. 7), half width of pulse (Test No. 8), oscillation frequency (Test No. 9), and transfer speed of focusing point (Test No. 10). Nevertheless, those Test Nos. gave the result remaining in the range specified by equations (1), (2), and (3). The relative standard deviation of these analytical values was within 5% for all of them, though some of them exceeded 2%.

To the contrary, Test No. 11 of Comparative Examples did not satisfy the equations (1), (2), and (3), and Test No. 15 and 16 did not undergo gas purification nor preliminary treatment, and had the elements exceeding the relative standard deviation of 5%.

Conventional Example did not undergo gas purification nor preliminary treatment as in the case of Comparative Examples, and gave a large relative standard deviation of C which might be difficult to analyze, and gave a large relative standard deviation of P and S which existed at a slight amount and which were easily affected by contaminants.

EXAMPLE-2

The solid specimens of stainless steel, aluminum alloy, titanium alloy, and ceramic material, as well as carbon steel were analyzed.

Adding to ICP, the analysis employed microwave induction plasma (hereinafter referred to simply as "MIP") emission spectrometry, and atomic absorption (hereinafter referred to simply as "AA") analysis.

The MIP emission spectrometry used an MIP torch instead of the ICP torch which was used in Example 1, and used high purity $N_2$ gas as the carrier gas and the plasma gas. The purchased gas contained carbon monoxide of 1 ppm, carbon dioxide of 0.1 ppm, and methane of 0.1 ppm, so the gas was purified using a Zr getter as in Example 1 in advance. The preliminary treatment was applied as in the case of Example 1.

The AA method used Ar as the carrier gas, and acetylene and air as the gas for excitation flame.

Figure 10:
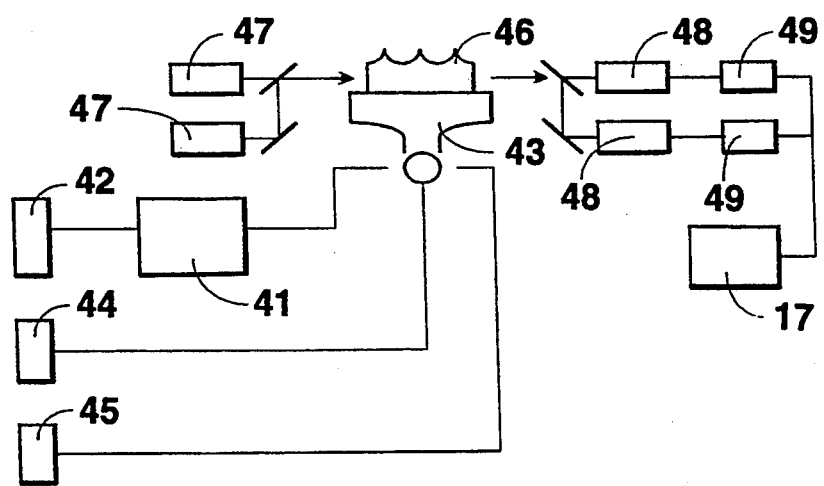
FIG. 10 shows a conceptual drawing of the laser vaporization device of atomic absorption analysis used in an Example of this invention.

FIG. 10 illustrates the device employed.

The reference number 41 indicates the fine particle generation section. The carrier gas is supplied to the section 41 from the gas cylinder 42. The fine particles generated by laser irradiation are sent to the burner 43. The reference numbers 44 and 45 indicate air cylinder and acetylene cylinder, respectively, to supply gases for excitation flame to the burner 43. The excitation flame is irradiated by the light containing the target wavelength from the cathode lamp 47. The spectrometer 48 receives the light to analyze spectra, and the detector 49 detects the degree of absorption of the target wavelength. The detected signals are sent to the data processing device 17 where the analytical values are calculated.

Two channels of measurement system are adopted to conduct an internal standard correction.

Both the gas for carrier gas and the gas for excitation flame used a commercial high purity gas without further purification. Since the target components were considered not being much affected by contaminants, the surface of original specimen was only machine-polished in air, and no preliminary treatment was applied.

The conditions of laser vaporization and the analytical result are summarized in Table 3.

All the elements analyzed gave a relative standard deviation within 2%.

This invention solved the problems on the quantity of fine particles generated from a solid specimen and on the representative characteristics of specimen by adjusting the conditions of laser ray irradiation and by adopting countermeasures to contamination of specimen. As a result, the invention allows an analysis of solid specimen promptly at a high accuracy. Accordingly, this invention provides a significant effect contributing to the improvement of quality of material produced, the elimination of waste of material, and the improvement of production efficiency.

TABLE 1

(A)

| Test Sample | Composition (wt. %) | | | | | |
|---|---|---|---|---|---|---|
| Carbon Steel | C | Si | Mn | P | S | B |
| | 0.25 | 0.20 | 0.65 | 0.01 | 0.01 | 0.001 |
| Stainless Steel | C | Ni | Cr | Mo | — | — |
| | 0.05 | 12.1 | 16.1 | 2.5 | — | — |
| Aluminum Alloy | Al | V | Fe | Cu | S | — |
| | 6.2 | 3.9 | 0.2 | 0.63 | 0.01 | — |

TABLE 1

(B)

| Test Sample | Composition (wt. %) | | | | |
|---|---|---|---|---|---|
| Titanium Alloy | Fe | Mg | Si | Cu | S |
| | 0.10 | 5.5 | 0.82 | 0.63 | 0.01 |
| Copper Alloy | Be | Cd | Fe | — | — |
| | 1.89 | 0.03 | 0.05 | — | — |
| Silicon Nitride | Al | Fe | — | — | — |
| | 0.18 | 0.15 | — | — | — |

TABLE 2

(B)

| | Test No. | Laser | Results of Analysis Relative Standard Deviation (%) | | | | | |
|---|---|---|---|---|---|---|---|---|
| | | | C | Si | Mn | P | S | B |
| Examples of Present Invention | 1 | NY | 1.5 | 1.0 | 0.8 | 1.2 | 0.8 | 1.6 |
| | 2 | NY | 2.0 | 1.3 | 0.8 | 1.8 | 1.9 | 2.2 |
| | 3 | NY | 1.8 | 1.2 | 1.1 | 1.0 | 1.5 | 1.7 |
| | 4 | NY | 1.5 | 1.3 | 1.2 | 1.7 | 1.8 | 1.9 |
| | 5 | NY | 0.9 | 0.6 | 0.4 | 0.7 | 0.8 | 1.4 |
| | 6 | NY | 1.9 | 1.5 | 0.9 | 1.5 | 1.7 | 1.8 |
| | 7 | NY | 4.7 | 4.1 | 3.1 | 4.6 | 4.7 | 5.0 |
| | 8 | NY | 4.5 | 2.3 | 1.8 | 3.5 | 3.2 | 3.8 |
| | 9 | RU | 4.3 | 2.1 | 2.3 | 3.8 | 4.2 | 4.7 |
| | 10 | NY | 2.8 | 1.8 | 1.1 | 1.8 | 1.9 | 2.2 |
| Comparative Examples | 11 | EX | 25 | 10 | 8.3 | 15 | 18 | 14 |
| | 12 | CG | 8.2 | 7.1 | 5.6 | 7.6 | 11.5 | 9.5 |
| | 13 | CG | 15 | 7.5 | 10 | 13 | 14 | 26 |
| | 14 | CG | 5.2 | 2.3 | 1.8 | 4.5 | 3.9 | 8.5 |
| | 15 | CG | 80 | 6.2 | 4.3 | 7.7 | 6.7 | 12 |
| | 16 | CG | 45 | 1.8 | 0.9 | 5.9 | 4.5 | 4.8 |
| Prior Arts | 17 | NY | 85 | 1.7 | 0.5 | 12 | 6.5 | 4.3 |

Notes
NY: Nd-YAG laser RU: Ruby laser CG: CO gas laser EX: exima laser

TABLE 2

(A)

| | Test No. | Laser | Laser Vaporaization | | | | Gas Purification and Preliminary Treatment | Selection Ratio (%) | | Rate of Particle Generation (μg/sec) |
|---|---|---|---|---|---|---|---|---|---|---|
| | | | Half Width of Pulse (μsec) | Energy Density (GW/cm²) | Frequency of Laser (Hz) | Moving Speed of Focus (mm/sec) | | Mn | Mo | |
| Examples of Present Invention | 1 | NY | 0.11 | 4 | 1000 | 50 | yes | 1.3 | 0.5 | 20 |
| | 2 | NY | 0.05 | 5 | 5000 | 0.1 | yes | 1.2 | 0.7 | 1 |
| | 3 | NY | 0.50 | 5 | 1000 | 50 | yes | 1.5 | 0.3 | 40 |
| | 4 | NY | 0.11 | 0.01 | 1000 | 50 | yes | 1.3 | 0.4 | 5 |
| | 5 | NY | 0.11 | 50 | 10000 | 100 | yes | 1.2 | 0.7 | 80 |
| | 6 | NY | 0.11 | 10 | 100 | 10 | yes | 1.3 | 0.5 | 10 |
| | 7 | NY | 0.50 | 0.005 | 10000 | 100 | yes | 1.1 | 0.9 | 0.1 |
| | 8 | NY | 0.007 | 20 | 500 | 0.1 | yes | 1.1 | 0.9 | 0.5 |
| | 9 | RU | 0.5 | 0.1 | 1 | 0.1 | yes | 1.3 | 0.5 | 0.5 |
| | 10 | NY | 0.11 | 5 | 10000 | 0.05 | yes | 1.2 | 0.7 | 5 |
| Comparative Examples | 11 | EX | 0.015 | 0.05 | 100 | 0.1 | yes | 1.1 | 0.8 | 0.05 |
| | 12 | CG | ∞ | 0.01 | 0 | 1 | yes | 10 | 0.02 | 20 |
| | 13 | CG | 0.11 | 0.005 | 1000 | 50 | yes | 4 | 0.2 | 0.01 |
| | 14 | CG | 0.11 | 4 | 10 | 50 | yes | 1.4 | 0.4 | 0.3 |
| | 15 | CG | 0.11 | 4 | 5000 | 0 | no | 1.2 | 0.7 | 0.1 |
| | 16 | CG | 0.11 | 4 | 1000 | 50 | no | 1.3 | 0.5 | 15 |
| Prior Art | 17 | NY | 0.15 | 1 | 5000 | 10 | no | 1.3 | 0.4 | 50 |

Notes:
NY: Nd-YAG laser RU: Ruby laser CG: CO gas laser EX: exima laser

TABLE 3

(A)

| Test Sample | Test No. | Laser Vaportion | | | | Gas Purification and Preliminary Treatment | Detection Method |
|---|---|---|---|---|---|---|---|
| | | Half Width of Pulse (μsec) | Energy Density (GW/cm²) | Frequency of Laser (Hz) | Frequency of Laser (mm/sec) | | |
| Carbon Steel | 31 | 0.11 | 5 | 1000 | 10 | yes | MIP |
| | 32 | 0.11 | 15 | 5000 | 10 | yes | |
| Stainless Steel | 33 | 0.11 | 5 | 1000 | 10 | yes | MIP |
| | 34 | 0.11 | 15 | 5000 | 10 | yes | |
| | 21 | 0.11 | 4 | 1000 | 50 | yes | |
| | 22 | 0.05 | 5 | 5000 | 50 | yes | |
| Aluminum Alloy | 23 | 0.50 | 50 | 1000 | 1 | yes | ICP |
| | 24 | 0.11 | 10 | 5000 | 1 | yes | |
| Titanium Alloy | 25 | 0.11 | 4 | 1000 | 10 | yes | ICP |
| | 26 | 0.05 | 10 | 100 | 100 | yes | |
| Silicon Nitride | 27 | 0.11 | 0.01 | 100 | 0.1 | yes | ICP |
| | 28 | 0.05 | 5 | 1000 | 10 | yes | |

TABLE 3-continued

| Test Sample | Test No. | (A) Laser Vaportion | | | | Gas Purification and Preliminary Treatment | Detection Method |
|---|---|---|---|---|---|---|---|
| | | Half Width of Pulse ($\mu$sec) | Energy Density (GW/cm$^2$) | Frequency of Laser (Hz) | Frequency of Laser (mm/sec) | | |
| Copper | 41 | 0.11 | 4 | 1000 | 10 | yes | AA |
| Alloy | 42 | 0.05 | 20 | 10000 | 10 | yes | |

TABLE 3

| Test Sample | Test No. | (B) Results of Analysis Relative Standard Deviation (%) | | | | |
|---|---|---|---|---|---|---|
| Carbon | | C | Si | Mn | P | S |
| Steel | 31 | 1.9 | 1.5 | 1.2 | 1.8 | 1.5 |
| | 32 | 1.7 | 1.4 | 1.0 | 1.8 | 0.9 |
| Stainless | | C | Ni | Cr | Mo | — |
| Steel | 33 | 1.9 | 0.6 | 0.7 | 1.2 | — |
| | 34 | 1.8 | 0.3 | 0.6 | 1.3 | — |
| | 21 | 1.9 | 0.3 | 0.6 | 0.8 | — |
| | 22 | 2.0 | 0.4 | 0.5 | 0.7 | — |
| Aluminum | | Al | V | Fe | — | — |
| Alloy | 23 | 0.8 | 0.4 | 1.4 | — | — |
| | 24 | 1.0 | 0.8 | 1.2 | — | — |
| Titanium | | Fe | Mg | Si | Cu | — |
| Alloy | 25 | 1.5 | 1.3 | 1.8 | 0.9 | — |
| | 26 | 1.8 | 1.5 | 1.7 | 1.2 | — |
| Silicon | | Al | Fe | — | — | — |
| Nitride | 27 | 1.5 | 1.8 | — | — | — |
| | 28 | 0.8 | 1.0 | — | — | — |
| Copper | | Be | Cd | Fe | — | — |
| Alloy | 41 | 1.0 | 1.8 | 0.9 | — | — |
| | 42 | 0.8 | 1.5 | 1.2 | — | — |

What is claimed is:

1. A method for analyzing solid sample comprising the steps of:

positioning a solid sample in a cell;

introducing an inert carrier gas into the cell, said carrier gas having a carbon content of 1 ppm or less as impurity;

a preliminary treatment step of irradiating laser beam to a sample surface of the solid sample in the inert carrier gas, said laser beam having a pulse half width of 0.001 $\mu$sec or more, a pulse energy density of 0.001 GW/cm$^2$ or more, and a frequency of 100 Hz or more;

generating fine particles in the inert carrier gas on a condition that a rate of fine particles generation, V ($\mu$g/sec), and selection ratio, S, satisfy the following equations, the selection ratio being a ratio of a concentration of a target element for analysis within the fine particles to a concentration of the target element for analysis within the solid sample;

$$S \leq 0.25 \log V + 1.5,$$

$$S \geq -0.2 \log V + 0.6,$$

$$0.1 \leq V \leq 100$$

intoducing the generated fine particles to a detector; and analyzing the concentration of the target element within the fine particles.

2. The method of claim 1, wherein the step of generating fine particles is carried out by irradiating laser beam having a pulse half width of 0.05–0.5 $\mu$sec, a pulse energy density of 0.01–50 GW/cm$^2$, and a frequency of 100 Hz or more.

3. The method of claim 2, wherein the laser beam is irradiated while moving a focusing point of the laser beam at a speed of 0.1 mm/sec or more in parallel to the sample surface.

4. The method of claim 3, wherein the moving of the focusing point is carried out by moving a forcusing lens in parallel to the sample surface.

5. The method of claim 3, wherein the moving of the focusing point is carried out by rotating a reflection mirror.

6. The method of claim 1, wherein the inert carrier gas is a gas purified by a getter gas purification device.

7. The method of claim 1, wherein the inert carrier gas is introduced to the cell through a gas piping system which is made of at least one selected from the group consisting of metal and glass.

* * * * *